United States Patent [19]
Lotvin et al.

[11] Patent Number: 5,888,798
[45] Date of Patent: Mar. 30, 1999

[54] CHONDROITINASE I AND CHONDROITINASE II PRODUCING MUTANTS OF P. VULGARIS

[75] Inventors: Jason Arnold Lotvin, Union, N.J.; Kiran M. Khandke, Nanuet; Mark E. Ruppen, Garnerville, both of N.Y.

[73] Assignee: American Cyanamid Company, Wayne, N.J.

[21] Appl. No.: 476,261

[22] Filed: Jun. 7, 1995

[51] Int. Cl.⁶ .............................. C12N 9/88; C12N 1/20; C12N 1/21
[52] U.S. Cl. ................ 435/232; 435/252.1; 435/252.3; 435/243; 435/873
[58] Field of Search ................ 435/232, 252.3, 435/243, 873, 252.1

[56] References Cited

U.S. PATENT DOCUMENTS

| | | | |
|---|---|---|---|
| 4,696,816 | 9/1987 | Brown | 424/94.61 |
| 5,049,501 | 9/1991 | Katsuragi et al. | 435/199 |
| 5,198,355 | 3/1993 | Kikuchi et al. | 435/232 |
| 5,292,509 | 3/1994 | Hageman | 424/94.61 |
| 5,496,718 | 3/1996 | Hashimoto et al. | 435/232 |
| 5,498,536 | 3/1996 | Khandke | 435/200 |
| 5,525,500 | 6/1996 | Khandke et al. | 435/232 |

FOREIGN PATENT DOCUMENTS

| | | |
|---|---|---|
| 0 576 294 A2 | 12/1993 | European Pat. Off. . |
| 0 613 949 A2 | 9/1994 | European Pat. Off. . |
| 62-122588 | 6/1987 | Japan . |
| 698769 | 4/1994 | Japan . |
| 1067253 | 5/1967 | United Kingdom . |
| WO 94/25567 | 11/1994 | WIPO . |

OTHER PUBLICATIONS

Kitamikado et al., *Applied Microbiology*, 29:414–421, 1975.
Sato et al., *Applied Microbiology Biotechnol.*, 41:39–46, 1994.
Sato et al., *Agric. Biol. Chem.*, 50:1057–1059, 1986.
Yamagata et al. *J. Biol. Chem.*, 243:1523–1535, 1968.
Pharmacia (1974), *Affinity Chromatography, Principles and Methods,* Pharmacia Fine Chemicals, Uppsula, Sweden, pp. 56–57.
Salyers et al. (Aug. 1988), *Applied & Environmental Microbiology,* 54 (8): 1964–1969.
Glover, D.M., (1985), "DNA Cloning, vol. 1, A Practical Approach", pp. 49–77, IRL Press (Oxford).
Scopes (1982) Protein Purification. New York: Springer Verlag. pp. 197–199.
Guthrie et al., *J. Bacteriology* 164:510–515.
Studier et al. (1990), *Methods in Enzymology* 185:60–85.
Lathe (1985), *J. Mol. Biol.* 183:1–11.
Bowie et al. (1990), *Science* 247:1306–1310.
Demain et al. (ed.) Manual of Industrial Microbiology and Biotechnology. Washington D.C.: American Society for Microbiology (1986).

*Primary Examiner*—Rebecca E. Prouty
*Assistant Examiner*—Gabriele E. Bugaisky
*Attorney, Agent, or Firm*—Darby & Darby

[57] ABSTRACT

Mutant *Proteus vulgaris* strains are provided that, when grown in the absence of an exogenous chondroitinase I and II inducer, produce *P. vulgans* chondroitinase I and chondroitinase II proteins. The mutants typically produce chondroitinase I and II proteins in the absence of exogenous inducers and in amounts in excess of those produced by wild-type *P. vulgaris* strains induced with such inducers. Two classes of such mutants, Classes 1 and 2, are disclosed. Class 1 and class 2 mutants differ in the relative amounts of chondroitinases I and II produced when cells are grown in casamino acids—supplemented minimal medium. Additional phenotypic variants that release chondroitinase I protein into the culture medium are provided as well. Also contemplated is a method for producing *P. vulgaris* chondroitinase I and II proteins. The mutant cells described above are cultured in the absence of a conventional exogenous chondroitinase I and II inducer, after which the cells are harvested and chondroitinase I and II are recovered from the harvested cells. A method for in situ detection of chondroitinase I and II production by bacterial colonies is also provided.

25 Claims, No Drawings

CHONDROITINASE I AND CHONDROITINASE II PRODUCING MUTANTS OF P. VULGARIS

TABLE OF RELATED CASES

| Ser. No. | Title | Filed | Status |
|---|---|---|---|
| 08/231,534 | Chromatographic Process for the Copurification of Chondroitinase I and II Proteins | April 22, 1994 | Pending |
| 08/232,540 | Novel Protein Designated Chondroitinase II and its Use With a Protein Designated Chondroitinase I to Achieve Complete Vitreal Disinsertion | April 22, 1994 | Pending |
| 08/233,008 | Methods for the Isolation and Purification of the Recombinantly Expressed Chondroitinase I and II Enzymes from P. Vulgaris | April 22, 1994 | Pending |
| 08/233,604 | Cloning and Expression of the Chondroitinase I and II Genes from P. Vulgaris | April 22, 1994 | Pending |
| PCT US94/04495 | Cloning and Expression of the Chondroitinase I and II Genes from P. Vulgaris | November 10. 1994 (Publication Date) | Pending |
| Not Yet Assigned (Atty. Docket No. 1B017-US1) | Copurification of Chondroitinase I and Chondroitinase II | April 24, 1995 | Pending |
| Not Yet Assigned (Atty. Docket No. 1B017-US2) | Compositions of Chondroitinase I and Chondroitinase II | April 24, 1995 | Pending |
| Not Yet Assigned (Atty. Docket No. 1B017-US3) | Method of Disinsertion of Vitreous Body from Neural Retina of the Eye | April 24, 1995 | Pending |
| Not Yet Assigned (Atty. Docket No. 1B017-US4) | Chondroitinase II | April 24, 1995 | Pending |
| Not Yet Assigned (Atty. Docket No. 1B017-US5) | Compositions of Isolated Chondroitinase I and Isolated Chondroitinase II | April 24, 1995 | Pending |
| Not Yet Assigned (Atty. Docket No. 1B017-US6) | Method of Disinsertion of the Vitreous Body from the Neural Retina of the Eye with Isolated Chondroitinase I and Isolated Chondroitinase II | April 24, 1995 | Pending |
| Not Yet Assigned (Atty. Docket No. 2B017-WO) | Chondroitinases I and II, Methods of Preparation, and Uses Thereof | April 24, 1995 | Pending |
| Not Yet Assigned (Atty. Docket No. 0646/0B122) | Chondroitinase Production in Recombinant Proteus Vulgaris Strains | Concurrently Herewith | Pending |

FIELD OF THE INVENTION

This invention relates to the preparation, identification, and isolation of mutant *Proteus vulgaris* cells that produce chondroitinase I and chondroitinase II proteins in the absence of natural exogenous inducers such as chondroitin sulfate.

BACKGROUND OF THE INVENTION

Chondroitinases are enzymes of bacterial origin that act on chondroitin sulfate, a component of the proteoglycans that mediate the attachment between the retina and the vitreous body of the human eye. Examples of chondroitinase enzymes are chondroitinase ABC, which is produced by the bacterium *Proteus vulgaris* (*P. vulgaris*), and chondroitinase AC, which is produced by *A. aurescens*. Chondroitinases ABC and AC function by degrading polysaccharide side chains in protein-polysaccharide complexes, without degrading the protein core.

Yamagata et al. (*J. Biol. Chem.* 243:1523–1535, 1968) describe the purification of the chondroitinase ABC from extracts of *P. vulgaris*. This enzyme selectively degrades the glycosaminoglycans chondroitin-4-sulfate, dermatan sulfate, and chondroitin-6-sulfate (also referred to respectively as chondroitin sulfates A, B, and C which are side chains of proteoglycans) at pH 8 at higher rates than it degrades chondroitin or hyaluronic acid. The products of the degradation are high molecular weight unsaturated oligosaccharides and an unsaturated disaccharide. However, chondroitinase ABC does not act on keratosulfate, heparin or heparitin sulfate.

Uses of chondroitinases include rapid, specific and non-surgical disruption of the attachment of the vitreous body to the neural retina of the eye, thereby facilitating removal of the vitreous body. See, for example, Hageman, U.S. Pat. No. 5,292,509.

Chondroitinase ABC is designated as chondroitinase I in the present invention. *P. vulgatis* chondroitinase I migrates with an apparent molecular mass of about 110 kDa when resolved by SDS-PAGE. The appearance of a doublet in SDS-PAGE resolution of chondroitinase I has been reported (Sato et al., *Agric. Biol. Chem.* 50:4,1057–1059, 1986). However, this doublet represents intact chondroitinase I and a 90 kDa degradation product (U.S. patent application Ser. Nos. 08/431,068; 08/428,949; 08/428,946; 08/428,948; 08/428,945; and 08/428,947, filed Apr. 24, 1995, (Atty Dock. Nos. 0646/1B017US1-0646/1B017US6) now pending). Commercial chondroitinase I protein preparations contain variable amounts of this 90 kDa degradation product and an additional 18 kDa degradation product also derived from chondroitinase I.

Another chondroitinase, chondroitinase II, has also been isolated and purified from *P. vulgaris*. Chondroitinase II is a polypeptide of 990 amino acids with an apparent molecular mass by SDS-PAGE of about 112 kDa. Its molecular mass as determined by electrospray and laser desorption mass spectrometry is $111{,}772 \pm 27$ and $111{,}725 \pm 20$ daltons, respectively. Chondroitinase II has an isoelectric point of 8.4–8.45. Its enzymatic activity is distinct from, but complementary to, that of chondroitinase I. Chondroitinase I endolytically cleaves proteoglycans to produce end-product disaccharides, as well as at least two other products which are thought to be tetrasaccharides. Chondroitinase II digests at least one of these tetrasaccharide products of chondroitinase I digestion of proteoglycan.

Native or wild-type *P. vulgaris* bacterial strains typically do not produce significant amounts of chondroitinases I and II under ordinary growth conditions. Wild-type strains of *P. vulgaris* can be induced to produce detectable levels of chondroitinase by providing an inducing substrate, such as chondroitin sulfate, as the sole carbon source. However, chondroitin sulfate, which is obtained from shark cartilage, is expensive and available only in limited quantities. Alternatively, cloned chondroitinase I and II genes in *E. coli* can be expressed using a heterologous expression system with an artificial inducer, which also increases the cost of chondroitinase I and II production.

Thus, there is a need in the art for *P. vulgaris* chondroitinase I and II production that does not require exogenous inducers.

SUMMARY OF THE INVENTION

Mutant *Proteus vulgaris* strains are provided that, when grown in the absence of an exogenous chondroitinase I and II inducer, produce *P. vulgaris* chondroitinase I and chondroitinase II proteins. The mutants of the present invention typically produce chondroitinase I and II proteins in the absence of exogenous inducers and in amounts in excess of those produced by wild-type *P. vulgaris* strains induced with such inducers. Two classes of such mutants, Classes 1 and 2, are disclosed. Class 1 and class 2 mutants differ in the relative amounts of chondroitinases I and II produced when cells are grown in casamino acids—supplemented minimal medium. Additional phenotypic variants that release chondroitinase I protein into the culture medium are provided as well.

Also contemplated is a method for producing *P. vulgaris* chondroitinase I and II proteins. The mutant cells described above are cultured in the absence of a conventional exogenous chondroitinase I and II inducer, after which the cells are harvested and chondroitinase I and II are recovered from the harvested cells.

A method for in situ detection of chondroitinase I and II production by bacterial colonies is also provided. The method comprises:

(a) culturing the colonies on a membrane filter on a first semi-solid bacterial growth medium;

(b) transferring the colony-containing filter to a second semi-solid bacterial medium, wherein the second medium comprises chondroitin sulfate;

(c) incubating the filter on the second medium for a sufficient time and at an appropriate temperature to allow digestion of chondroitin sulfate in the vicinity of each of the colonies;

(d) removing the filter from the second medium;

(e) contacting the second medium with a solution containing an agent capable of causing the precipitation of chondroitin sulfate within the medium; and (f) visually observing the second medium, wherein appearance of a zone lacking the chondroitin sulfate precipitation signifies the chondroitinase I production.

The constitutive mutant *P. vulgaris* strains isolated according to the present invention are used to produce large amounts of chondroitinases I and II in a cost-effective manner. These proteins may be used in analytical and clinical procedures, including non-surgical disruption of chondroitin sulfate-containing tissues, such as, for example, in non-surgical disinsertion of the vitreous body from the neural retina of the eye.

DETAILED DESCRIPTION OF THE INVENTION

Chondroitinase I and Chondroitinase II

Chondroitinase I and chondroitinase II are enzymes produced by *P. vulgaris* that catalyze the breakdown of chondroitin sulfate, including that present in proteoglycans. The physical and enzymatic characteristics of each enzyme are summarized in Table 1.

TABLE 1

Chondroitinase I Protein and Chondroitinase II Protein

| | 110 kDa | 112 kDa |
|---|---|---|
| SDS-PAGE molecular weight | ~110,000 daltons | ~112,000 daltons |
| Electrospray mass spectrometry | 112,527 ± 25 daltons | 111,772 ± 27 daltons |
| Laser desorption mass spectrometry | 112,508 ± 20 daltons | 111,725 ± 20 daltons |
| Isoelectric point/s | pH 8.35 and pH 8.45 | pH 8.45 |
| Amino acid composition | absence of cysteines, rich in serine | otherwise similar to 110 kDa |
| Release of di and oligosaccharides from chondroitin sulfate | +++ | — |
| Digestion of tetrasaccharides not digested by chondroitinase I | — | +++ |

Wild-Type *P. Vulgaris* Strains

Wild-type strains of *P. vulgaris* accumulate easily detectable levels of enzymatically active chondroitinases I and II only when grown in a culture containing an exogenous chondroitinase I and II inducer, such as chondroitin sulfate, as the sole carbon source. Growth of wild-type strains of *P. vulgaris* in media without such an inducer, such as, for example, in a rich medium containing many carbon sources or in a minimal medium containing, for example, glucose or another non-chondroitin carbon source as a sole carbon source, results in insignificant or no detectable accumulation of chondroitinase I or II activity.

Mutant *P. Vulgaris* Strains

The present invention encompasses mutant strains of *Proteus vulgaris* that produce *P. vulgaris* chondroitinase I and chondroitinase II enzymes in a constitutive manner. These mutants may include but are not limited to strains containing mutations in the promoter region or other regulatory regions of the chondroitinase genes, in the protein-coding region of the chondroitinase genes, or in the regulatory or protein-coding region of repressor or inducer genes that regulate chondroitinase expression. For example, these mutant strains may include exogenous chondroitinase I and II inducer-independent chondroitinase I and II genes as constituents of their genomes. Any of these mutants are constitutive mutants. These mutants produce or accumulate chondroitinase I and II proteins in the absence of one or more traditional exogenous chondroitinase inducer substances such as, for example, chondroitin sulfate, N-acetylgalactosamine, and active analogues thereof. The *P. vulgaris* mutant strains of the present invention produce high levels of chondroitinases I and II under normal growth conditions even in the absence of chondroitin sulfate or other traditional chondroitinase inducers.

Characterization

The mutant strains include the classes and subclasses described below and are characterized with respect to the absolute and relative amounts of chondroitinase I and chondroitinase II proteins and enzymatic activity that they produce. The amounts of chondroitinase I and chondroitinase II proteins can be measured by any method well-known in the art, such as, for example, SDS-PAGE followed by immunoblotting, radioimmunoassay, ELISA, and the like.

The enzymatic activity of chondroitinase I can be quantified by measuring the degradation products produced by the action of the enzyme on chondroitin sulfate, which are preferably detected by their distinctive ultraviolet absorbance properties. If required, the products are resolved by any useful method, including without limitation one-dimensional and two-dimensional thin layer chromatography, and gel permeation chromatography (GPC). The action of chondroitinase I on chondroitin sulfate or proteoglycans produces disaccharides and an unsaturated disulfated tetrasaccharide that is a substrate for chondroitinase II. Thus, in a preferred embodiment, chondroitinase II activity is measured by monitoring the digestion of this tetrasaccharide into disaccharides using high performance liquid chromatography (HPLC).

A typical chondroitinase I assay is conducted by incubating the enzyme preparation with a solution of 0.5 mg/ml chondroitin C sulfate in Tris acetate buffer, pH 8.0. After incubation at 37° C. for 20 sec, the absorbance of the reaction mixture at 232 nm (which represents the absorbance of the newly introduced double bond between carbon 4 and 5 of the D-glucuronic acid at the non-reducing end of the disaccharide reaction product) is measured at 30-second intervals for at least 2 minutes and compared with that of control reactions lacking or containing chondroitinase I.

For chondroitinase II assays, the tetrasaccharide substrate at a concentration of 0.2–20 mg/ml is incubated with a source of enzyme at 10°–50° C., preferably 37° C., for an appropriate time, such as 15 minutes. The reaction products are then separated by any suitable chromatographic method, including without limitation gel permeation, anion exchange, hydrophobic interaction, and reverse-phase chromatography (all preferably performed using HPLC). The disaccharide product is measured by any suitable technique such as, for example, measuring the absorbance at a given wavelength, mass spectrometry, conductivity, refractive index and viscosity, and comparison to standards purified earlier and identified by TLC and other methods. It is often preferred to measure the absorbance at 232 nm. One unit of chondroitinase II is the quantity of enzyme that catalyzes the formation of 1 micromole of disaccharide product from the tetrasaccharide per minute at 37° C., pH 8.0.

For analysis of constitutive mutants, bacterial cells are harvested from an exponential culture, washed, and disrupted by pressure, after which cellular debris is removed by centrifugation and enzymatic assays are performed using the supernatants as sources of chondroitinase enzymes.

The mutant *P. vulgaris* cells of the present invention preferably produce chondroitinase I at levels of at least 0.2 chondroitinase I enzymatic activity units per $A_{600}$ unit of bacterial culture. A unit of chondroitinase I activity is the quantity of protein that catalyzes the formation of 1 micromole of unsaturated disaccharide from chondroitin sulfate per minute at 37° C., pH 8.0. One $A_{600}$ unit of bacterial culture, representing the absorbance at 600 nm, corresponds to approximately $10^8$ cells. Most preferably, constitutive mutant cells produce at least 0.5 enzymatic activity units of chondroitinase I per $A_{600}$ unit of bacterial culture. Typically, constitutive mutant cells express chondroitinase I and II enzymatic activities in ratios of from about 50:50 to 80:20 (I:II). Thus, constitutive mutant cells preferably contain at least about 0.125 to about 0.5 enzymatic activity units of chondroitinase II per 1 $A_{600}$ unit of bacterial culture.

Constitutive mutants preferably exhibit normal growth rates in fermentor cultures, and, in general, aside from their constitutive production of chondroitinases I and II, possess a normal phenotype relative to wild-type cells.

Class 1, Class 2, and Subclass Mutant *P. Vulgaris* Strains

Two phenotypically distinct major classes of *P. vulgaris* mutants have been identified using the chondroitinase I assay described above. Class 1 mutants (for example, ATCC #55691 (a) produce substantially about as much chondroitinase I, when grown on rich medium (for example, 20-10-5 medium) in the absence of an exogenous chondroitinase I and II inducer, as does wild-type *P. vulgaris* (for example, ATCC #6896) grown on the same medium supplemented with a chondroitinase I and II inducive amount of the inducer, and (b) produce a greater amount of, and preferably approximately twice as much, chondroitinase I, when grown in casamino acid-supplemental glucose minimal medium in the absence of the inducer, than does the mutant cell when grown in rich medium in the absence of the inducer and also substantially more than wild-type *P. vulgaris* grown in casamino acid-supplemented minimal medium containing chondroitin sulfate. Class 2 mutants (for example, ATCC #55689 and 55690) produce about half the chondroitinase I than a Class 1 mutant produces when grown in casamino acid-supplemented minimal medium in the absence of an exogenous chondroitinase I and II inducer, but about the same chondroitinase I levels as a Class 1 mutant when grown in rich medium in the absence of the inducer.

Additionally, phenotypic subclass variation was observed among different Class I isolates. These strains exhibited differences in the relative distribution of chondroitinase activity between the cells and the culture medium. Typically in wild-type and many mutant *P. vulgaris* strains, chondroitinases I and II are exported into the periplasmic space, but little chondroitinase I or II activity is actually secreted into the culture medium. Some Class 1 isolates retain this distribution pattern. However, a subclass of the Class 1 strains export or release into the culture medium up to 30% of the total chondroitinase I produced.

Isolation of Mutant Strains

Mutant strains of *P. vulgaris* according to the present invention may be prepared by (a) mutagenizing a *P. vulgaris* culture and (b) subjecting the mutagenized population of cells to a screening or selection procedure that identifies colonies that produce chondroitinases in the absence of chondroitin sulfate or N-acetylgalactosamine.

Mutagenesis

Mutagenesis may be accomplished by exposure of wild-type or previously mutagenized cells to any appropriate mutagens, including, but not limited to, N-methyl-N'-Nitro-N-nitrosoguanidine; hydroxylamine; 4-Nitroquinoline-1-oxide; ethyl methanesulfonate; methyl methanesulfonate; and ultraviolet light. Mutagenesis is carried out using methods that are well-known in the art, such as described in Demain et al., *Manual of industrial Microbiology and Biotechnology*, American Society for Microbiology (1986). Preferably, N-methyl-N'-Nitro-N-nitrosoguanidine is used as a mutagen.

For example, an exponentially growing culture of *P. vulgaris* can be exposed to nitrosoguanidine at concentrations ranging from 30–500 μg/ml at 37° C. for about 5 to about 20 minutes, after which the culture medium is replaced with nitrosoguanidine-free medium. The cells are then incubated at 37° C. for one to several hours to allow for fixation and segregation of mutations. The cultures are then stored at −70° C. as glycerol stocks.

Screening

Mutagenized cultures are subjected to screening or selection procedures to identify cells in which the normal regulation of chondroitinases I and II expression no longer functions, i.e., cells that produce high levels of chondroitinases I and II even when an exogenous inducer, such as, for example, chondroitin sulfate and/or N-acetylgalactosamine, is not present in the culture environment. Selection procedures useful in practicing the present invention include, but are not limited to, any procedure that results in the selective survival of the mutant chondroitinase-producing cells as defined above over wild-type cells in the same culture.

Preferably, screening procedures are used to identify rare constitutive chondroitinases I and II-producing cells from among a large background of wild-type cells. Useful in situ screening procedures include, without limitation, those that detect colonies that either bind chondroitinase-specific antibodies or that catalyze the breakdown of chondroitin sulfate or proteoglycan. Colony immunoblotting assays use well-known methods such as those disclosed in, for example, Harlow and Lane, *Antibodies, A Laboratory Manual*, Cold Spring Harbor Laboratory (1988). Detection assays that depend on chondroitinase enzymatic activity include, without limitation, the chondroitin depletion method described below and colorimetric assays that detect chondroitin or chondroitin hydrolysis. Either screening method (immunoblotting and chondroitin depletion) can be used at any of the stages in initial identification and subsequent colony purification of constitutive mutant cells.

Antibody Screening

In one embodiment, an antibody-based screening method is used to identify *P. vulgaris* colonies that produce chondroitinases I and II even when an exogenous inducer such as, for example, chondroitin sulfate is absent from the culture medium as follows:

(1) Mutagenized *P. vulgaris* cultures are seeded onto filters that are placed onto agar plates containing either rich or minimal medium lacking an exogenous inducer such as chondroitin sulfate and/or N-acetylgalactosamine. The filters may comprise nylon, paper, nitrocellulose, or polyvinylidene difluoride, preferably NYTRAN (Schleicher and Scheull, Keene, N.H.). The optimum colony density for this step is about 1000 per plate.

(2) The filters are then transferred from the plates to a solution that permeabilizes and lyses the cells on the filter, so that chondroitinase polypeptides are released from the cells and become fixed to the filter.

(3) The filters are then incubated with specific antibodies directed against chondroitinase I and/or chondroitinase II, such as, for example, goat anti-chondroitinase I antibody and/or rabbit anti-chondroitinase II antibody.

(4) Finally, specifically bound antibody is detected using any enzymatic, fluorescent, radioactive, or other detection means well known in the art.

Goat anti-chondroitinase I antibodies are prepared by (a) purifying *P. vulgaris* chondroitinase I from an *E. coli* strain that expresses chondroitinase I from an overexpression plasmid (as disclosed in U.S. patent application Ser. No. 08/233,008, filed Apr. 22, 1994); and (b) mixing the purified chondroitinase I with Freud's adjuvant and inoculating the resulting emulsion into goats. Procedures for the purification and analysis of antibodies are those well-known in the art. Rabbit anti-chondroitinase II antibodies are prepared similarly.

In a preferred embodiment of the antibody screen, *P. vulgaris* colonies are grown on Nytran filters that are placed onto agar plates containing "20-10-5" medium, which includes 20 g/l tryptone, 10 g/l yeast extract, and 5 g/l NaCl. After spraying the bacterial colony-containing filters with a solution of bovine serum albumin to block background sites, the filters are floated on liquid chloroform or placed on chloroform-saturated filter paper for several hours, releasing chondroitinases and binding them to the filter in the immediate vicinity of chondroitinase-producing colonies. The washed filters are then incubated sequentially with (1) goat anti-chondroitinase I antibodies; (2) peroxidase-conjugated rabbit anti-goat antibody (BioRad); and (3) color reagents to visualize filter-bound peroxidase (BioRad). In parallel, colony-purified wild-type *P. vulgaris* cells are grown on medium lacking and containing chondroitin sulfate to serve as negative and positive controls, respectively, for the screening procedure.

Colonies that display detectable amounts of chondroitinases I and/or II using this assay are picked, diluted, re-inoculated on plates, and the entire detection procedure is repeated. Several cycles of colony purification are performed in this manner, until a pure culture of each individual mutant strain is obtained.

Chondroitin Depletion Screening Assay

In another embodiment, a chondroitin depletion assay is used to identify chondroitinase I and II-producing colonies. In this procedure, mutagenized *P. vulgaris* cultures are seeded onto filters as described above, and the filters are placed onto agar plates containing either rich or minimal medium lacking chondroitin sulfate. After overnight growth, the filters are transferred to plates containing agar supplemented with 5 mg of chondroitin sulfate/ml and a protein synthesis inhibitor at a concentration effective to inhibit protein synthesis on the filter-bound bacterial colonies, preferably 100 μg/ml tetracycline. After incubation for about 4 to about 8 hours, the filters are removed, and the plates are flooded with about 10 ml each of 0.5% cetyl pyridinium chloride (Sigma Chemical Co., St. Louis, Mo.). This treatment causes chondroitin sulfate to form a cloudy precipitate within the agar. Constitutive mutant colonies that elaborate chondroitinase I produce an obvious clear zone surrounding the colony that is easily visualized by eye.

Transformed Constitutive Mutants

It may be desirable to increase the production of chondroitinases I and II further over that seen in the constitutive mutants isolated as described above, or selectively to increase or decrease the production of chondroitinase I or chondroitinase II. For this purpose, constitutive mutant strains isolated and characterized as described above can be further modified by transformation with DNA plasmids encoding, for example, chondroitinase I and/or chondroitinase II, under the control of the native chondroitinase promoter or a heterologous promoter. The genes encoding both chondroitinase I and chondroitinase II proteins are present on a *P. vulgaris* genomic DNA sequence of about 30 kb in length, which is contained within a cosmid clone designated $LP^2$-751 (see Example 1 below). DNA encoding *P. vulgaris* chondroitinase I and/or chondroitinase II protein (s) can be cloned into a plasmid that replicates in *P. vulgaris* cells. Other plasmids may encode regulatory or other proteins that alter the transcriptional or translational steps in chondroitinase expression. Suitable plasmid vectors are provided in concurrently U.S. Ser. No. 08/481,179 (attorney docket no. 0646/0B122).

Alternatively, the constitutive mutant cells may be subjected to insertional mutagenesis to selectively inactivate the chromosomal chondroitinase I or chondroitinase II gene. Any of these manipulations are well-known in the art of recombinant DNA technology.

Purification

The chondroitinase I and II enzymes produced by a constitutive mutant may be co-purified to homogeneity (i.e., to obtain a pure mixture of chondroitinase I and II) and the co-purified enzymes are suitable for use in, for example, vitreal disinsertion.

Although a variety of methods can be used to isolate and purify native chondroitinases I and II, a preferred affinity chromatography method includes:

(a) preparing a clarified homogenate of mutant *P. vulgaris* cells, the homogenate having a pH of 5.8 to 7.4;

(b) loading the homogenate onto a negatively charged cation exchange resin chromatographic support so that any positively charged proteins comprising chondroitinase I and chondroitinase II in the homogenate form a non-covalent bond with the negatively charged support;

(c) affinity-eluting, in pools, the chondroitinase proteins from the support with an aqueous solution of chondroitin sulfate at a pH 7.0–9.5;

(d) loading the affinity eluted protein pools onto an anion exchange resin chromatographic support to yield an unbound eluate; and (e) recovering the chondroitinase I and chondroitinase II proteins in the unbound eluate.

The proteins can be further purified by metal chelating chromatography by (1) contacting the unbound eluate with a metal chelating affinity chromatography support to bind further the chondroitinase proteins;

(2) eluting with an appropriate solvent; and (3) recovering the chondroitinase proteins.

If desired, the copurified proteins can be separated from each other by additional process steps involving further cation exchange chromatography. The individually purified proteins can be used in ratios other than those obtained by the copurification procedure.

DESCRIPTION OF THE PREFERRED EMBODIMENTS

The following examples illustrate the present invention without limitation.

Procedure A
Preparation of Goat Anti-Chondroitinase I Antibody

Chondroitinase I isolated essentially as described above, which was 99.4% pure (as assessed by SDS-PAGE) was combined with complete Freund's adjuvant in a 1:1 (v/v) proportion and emulsified. For the initial immunization, 5 mg of chondroitinase I was inoculated into goats intradermally. At one-month intervals, the animals were boosted with progressively smaller amounts of chondroitinase I (1 mg, 500 µg, 250 µg) in incomplete Freund's adjuvant administered intramuscularly. The animals were bled every month, and the appearance of specific anti-chondroitinase I antibodies was assessed by Western blotting, which showed reactivity with a single protein band corresponding to chondroitinase I.

Procedure B
Preparation of Rabbit Anti-Chondroitinase II Antibody

A 1 mg/ml solution of chondroitinase II purified as described above is combined with complete Freund's adjuvant in a 1:1 (v/v) proportion and emulsified. 200–400 µg of the emulsion is inoculated into rabbits intradermally or subcutaneously. At 30 days, an emulsion comprising a 1:1 mixture of the chondroitinase II solution as above and incomplete Freund's adjuvant is prepared and inoculated into the rabbits as above. At 30-day intervals, the animals are bled, and the serum is tested for anti-chondroitinase II antibodies.

EXAMPLE 1
Isolation of Chondroitinase-Producing Mutants

The following procedure was used to isolate chondroitin-sulfate-independent chondroitinase-producing mutants of *P. vulgaris*.

A. Mutagenesis

Wild-type *P. vulgaris* cells (ATCC 6896, designated strain LL2289) were grown overnight at 37° C. in 10 ml of 20-10-5 medium. 5 ml of the overnight culture were inoculated into 100 ml of fresh 20-10-5 medium and were grown to a density of 1.3 $A_{600}$ units. The cells were recovered by centrifugation and were resuspended in fresh medium at a concentration of $4 \times 10^8$ cells/ml. Nitrosoguanidine (Sigma Chemical Co., St. Louis, Mo.) was added to 5 ml aliquots of the cells so that the final concentration of nitrosoguanidine was 30–500 µg/ml. Mutagenesis was for 10 min at 37° C. The cells were pelleted, resuspended in fresh medium, and grown at 37° C. for 2 hours to allow for fixation and segregation of mutations.

B. Immunoscreening

Mutagenized *P. vulgaris* cells were diluted and plated onto Nytran filters at a density of 2000 colonies/plate, and the filters were placed onto glucose-containing minimal medium agar plates. Fifty filters were plated and incubated at 30° C. for 24 hours. The filters were replica plated onto master agar plates containing 20-10-5 medium, which were incubated at 30° C. for 5 hours and then stored at 4° C. for later use.

The filters were sprayed with a solution of 7.5% (w/v) bovine serum albumin (Sigma Chemical Co., St. Louis, Mo.), and then were placed on chloroform-saturated absorbent paper for 2 hours to lyse the colonies and to fix the chondroitinase proteins to the filter. The filters were then placed on TE-saturated paper for 5 min (TE=10 mM Tris-HCl, pH 7.4, 1 mM EDTA). The lysed colonies were dislodged from the filters by repeatedly rinsing the filters in distilled water while blotting.

The filters were then incubated for 2 hours at 22° C. with goat anti-chondroitinase I antibody prepared according to Procedure A at a 1:5000 dilution in 10 mm Tris HCl, pH 7.4, 0.1% Tween-20, 1% Bovine Serum albumin, and 0.85% NaCl. The filters were then washed in the same buffer lacking albumin, after which horseradish peroxidase-conjugated rabbit anti-goat antibody was added at 1:4000 dilution (BioRad). After incubation at 22° C. for 2 hours, the filters were washed, and bound antibody was detected using the 4-chloro-naphthol reaction. Positive colonies appeared purple against a background of essentially colorless wild-type (non-chondroitinase-producing) colonies.

Thirty-six positive signals were observed in the immunoblot screen and aligned to the master plates. A region of the plate corresponding to the signal was recovered by plugging the appropriate area of the master plate with the wide end of a sterile pipette. The plug was placed into 3 ml glycerol and vortexed to dislodge the cells. The suspensions were divided into 3×1 ml portions and frozen at −70° C.

C. Colony Screening by Enzymatic Activity

Suspensions of cells identified as in Section B above were plated on Nytran filters as above. The filters were placed onto agar plates in rich agar 20-10-5 medium, and the plates were incubated at 30° C. overnight. The filters were transferred to agar plates containing 5 mg/ml chondroitin sulfate and 100 µg/ml tetracycline and incubated for 6 hours at 37° C.

The filters were then removed, and the plates were flooded with 10 ml each of a solution of 0.5% (v/v) cetyl pyridinium chloride (Sigma Chemcial Co., St. Louis, Mo.). Positive colonies produced a clear zone (indicating chondroitin depletion) in a background of white precipitate.

D. Results 100,000 P. vulgaris colonies were subjected to an initial screen using the colony immunoblotting technique described in section B above. Of these, 36 were found to be strongly positive, and 23 were judged intermediate in constitutive chondroitinase production.

The chondroitin depletion assay described above was used to identify positive colonies during subsequent rounds of colony purification. Three colonies, designated LL2485, LL2492, and LL2498, were chosen for further analysis (see below).

EXAMPLE 2

Comparison of Chondroitinase I and II Production in Constitutive Mutants

A shake flask fermentation analysis was performed on constitutive mutants identified as described in Example 1. The rich medium consisted of 20 g/l tryptone, 10 g/l yeast extract, and 5 g/l NaCl. The minimal medium consisted of 6.0 g/l $Na_2HPO_4$, 3.0 g/l $NaHPO_4$, 0.5 g/l NaCl, 1.0 g/l $NH_4Cl$, 4 g/l casamino acids, 0.2 g/l $MgSO_4$, 0.02 g/l $FeSO_4$-$7H_2O$, and 0.05 g/l nicotinic acid. Glucose-containing minimal medium had 5 g/l glucose; both chondroitin-sulfate-containing minimal medium and rich medium had 5 g/l chondroitin-6-sulfate.

0.2 ml of an overnight culture of each strain was inoculated into 5 ml of each growth medium. The cultures were incubated for 7 hours at 37° C., after which the absorbance of the cultures at 600 nm was measured. 3-ml aliquots of each culture were collected by centrifugation, and the cells were resuspended in 3 ml of 50 mM Tris-acetate, pH 8.0. The cells were then disrupted by two passages through a French Pressure mini-cell at 18,000 psi (SLM Instruments, Urbana, Ill.). The cell homogenates were then centrifuged at 12,800×g to remove cellular debris, and the supernatant was recovered and assayed for chondroitinase I activity. Some of the samples were also assayed for chondroitinase II activity. The results of the chondroitinase I assays are shown in Table 2 below.

TABLE 2

CHONDROITINASE I ACTIVITIES (units/$A_{600}$ of culture)

| STRAIN | DESCRIPTION | MINIMAL + GLUCOSE | MINIMAL + CHONDROITIN $SO_4$ | RICH | RICH + CHONDROITIN $SO_4$ |
|---|---|---|---|---|---|
| LL2289 | wild-type | 0* | 0.088 | 0* | 0.173 |
| LL2480 | wild-type | 0* | 0.269 | 0* | 0.153 |
| LL2485 | constitutive class I | 0.574 | 0.366 | 0.433 | 0.285 |
| LL2492 | constitutive class I | 0.927 | 0.490 | 0.602 | 0.423 |
| LL2498 | constitutive class II | 0.297 | 0.243 | 0.325 | 0.448 |

*not detectable

Example 2 demonstrates that Class 1 mutants show elevated chondroitinase I levels compared to chondroitin sulfate-induced wild-type cells, but produce even more chondroitinase I activity when grown on glucose minimal medium compared to chondroitin sulfate minimal medium. Class 2 mutants produce lower chondroitinase I levels than Class 1 mutants, but produce equivalent amounts of chondroitinase I on either glucose or chondroitin sulfate when evaluated in a minimal medium.

The proportion of chondroitinase I that remained associated with the cells relative to that released into the supernatant varied among the Class 1 mutants. Strain LL2492, for example, exhibited a distribution of 1.58:0.06 of cell-associated:supernatant activity. In contrast, strain LL2485 exhibited a cell:supernatant chondroitinase I distribution of 1.18:0.35, representing a five-fold increment in chondroitinase I activity released into the supernatant.

Strains LL2485 and LL2492 also express chondroitinase II independent of chondroitin sulfate induction. In one comparative study, strain LL2492 and the wild-type strain LL2480 were grown in glucose-containing minimal medium. No chondroitinases could be detected in the LL2480 culture, while strain LL2492 produced 1.17 U/ml chondroitinase I and 0.6 U/ml chondroitinase II. In a second study, wild-type strains LL2289 and LL2480 showed no detectable synthesis of chondroitinases when grown on glucose, while strain LL2485 produced 1.69 U/ml chondroitinase I and 1.39 U/ml chondroitinase II.

EXAMPLE 3

Transformation of Mutant Proteus Vulgas with a Chondroitinase I and II Expression Vector Proteus vulgaris strain LL2492 was transformed with a plasmid using the following procedure. An overnight culture of each strain was inoculated into 20-10-5 medium and incubated at 37° C. until the cultures reached an $A_{600}$ of 0.5. The cells were collected by centrifugation and repeatedly washed in cold distilled water; they were then concentrated 150-fold in cold 20% glycerol and stored frozen at −70° C.

Electroporation was performed using a BioRad Gene Pulser. 200 μl of washed cells were mixed with 1–10 μl of DNA (corresponding to 0.1–2.0 μg DNA) in a 0.2 cm cuvette and pulsed at 2.4 kilovolts using a 25μ Farad capacitor with a 200 Ohm resistor. The electroporated cells were then inoculated into 2 ml of 20-10-5 medium, and the cultures were incubated at 37° C. for about 75 min, after which they were plated on 20-10-5 agar containing 25 μg/ml chloramphenicol. After overnight incubation at 37° C., chloramphenicol-resistant colonies were observed. At least one colony of each transformant was streaked onto chloramphenicol agar. Individual colonies were then inoculated into 20-10-5 liquid medium containing 25 μg/ml chloramphenicol and grown overnight at 37° C. Glycerol was then added and the strains were stored at −70° C.

The plasmids used for transformation were pACYC184, pLP²-1521, and pLP²-1531. The P. vulgaris strains transformed with the plasmids were designated strains LL4119, LL4107, and LL4142, respectively.

EXAMPLE 4

Analysis of Chondroitinases I and II Production

The plasmid-transformed P. vulgaris strains prepared as in Example 3 above were analyzed for their production of chondroitinases I and II. The growth medium was casamino acid-supplemented minimal medium containing 25 μg/ml chloramphenicol. Incubations were performed at 30° C. and samples were taken at 7 and 24 hours after initiation of growth. The starting cell densities were $10^6$–$10^7$ cells/ml. In each case, cells were collected by centrifugation, disrupted in a French pressure cell, and subjected to chondroitinase enzymatic activity assays. The results, expressed as activity units/A600 units of the culture, are shown in Table 3.

TABLE 3

CHONDROITINASE I AND II PRODUCTION

| STRAIN | STRAIN BKGRND | PLASMID | 7 HOUR SAMPLE U/OD CHON I | 7 HOUR SAMPLE U/OD CHON II | 24 HOUR SAMPLE U/DO CHON I | 24 HOUR SAMPLE U/OD CHON II |
|---|---|---|---|---|---|---|
| LL2492 | LL2492 | NONE | 0.4 | 0.2 | 0.55 | 0.44 |
| LL4119 | LL2492 | pACYC184 | 0.41 | 0.13 | 0.6 | 0.46 |
| LL4107 | LL2492 | $LP^2$-1521 | 1.14 | 0.05 | 2.59 | 0.32 |
| LL4142 | LL2492 | $LP^2$-1531 | 1.39 | 0.72 | 3.96 | 1.93 |

All patents, applications, articles, publications, and test methods mentioned herein are hereby incorporated by reference.

Many variations of the present invention will suggest themselves to those skilled in the art in light of the above detailed description. Such obvious variations are within the full intended scope of the appended claims.

We claim:

1. A mutant *Proteus vulgaris* cell comprising at least one mutation in the genome of said cell, said mutation having the property of altering the expression of chondroitinase I and II, wherein said mutant cell, when grown in the absence of an exogenous chondroitinases I and II inducer, produces chondroitinase I protein and chondroitinase II protein.

2. A mutant cell as defined in claim 1, wherein said inducer is selected from the group consisting of chondroitin sulfate, N-acetylgalactosamine, and a combination thereof.

3. A mutant cell as defined in claim 2, wherein said inducer comprises chondroitin sulfate.

4. A mutant cell as defined in claim 1, wherein said mutant cell constitutively expresses said chondroitinases I and II proteins.

5. A mutant cell as defined in claim 1 comprising a class 1 mutant cell, wherein said Class 1 mutant cell:

(a) when grown in rich medium in the absence of an exogenous chondroitinases I and II inducer, produces substantially about the same amount of chondroitinase I as does a wild-type *Proteus vulgaris* cell grown in said rich medium further comprising a chondroitinases I and II inducive amount of said inducer; and (b) when grown in casamino acid-supplemented minimal medium in the absence of said inducer, produces a greater amount of chondroitinase I than does said mutant cell grown in rich medium in the absence of said inducer.

6. A mutant cell as defined in claim 5, wherein said inducer is selected from the group consisting of chondroitin sulfate, N-acetylgalactosamine or a combination thereof.

7. A mutant cell as defined in claim 6, wherein said inducer comprises chondroitin sulfate.

8. A mutant cell as defined in claim 5, wherein said mutant cell releases into a culture medium at least a portion of said produced chondroitinase I protein, chondroitinase II protein, or a combination thereof.

9. A mutant cell as defined in claim 8, wherein said mutant cell releases into said culture medium up to 30% by weight of the total chondroitinase I protein produced by said cell.

10. A mutant cell as defined in claim 1 comprising a Class 2 mutant cell, wherein said Class 2 mutant cell:

(a) when grown in casamino acid-supplemented minimal medium in the absence of an exogenous chondroitinases I and II inducer, produces less chondroitinase I than does a Class 1 mutant cell when grown in said casamino acid-supplemented minimal medium in the absence of said inducer; and (b) when grown in rich medium in the absence of said inducer, produces about the same amount of chondroitinase I protein as does a Class 1 mutant when grown in said rich medium in the absence of said inducer.

11. A mutant cell as defined in claim 10, wherein said inducer is selected from the group consisting of chondroitin sulfate, N-acetylgalactosamine, and a combination thereof.

12. A mutant cell as defined in claim 11, wherein said inducer comprises chondroitin sulfate.

13. A mutant cell as defined in claim 1, wherein said mutant cell produces chondroitinase I protein at a level of at least 0.2 chondroitinase I activity units per $A_{600}$ absorbance unit of bacterial culture.

14. A mutant cell as defined in claim 1, wherein said mutant cell produces said chondroitinase I and chondroitinase II proteins at a ratio of chondroitinase I:chondroitinase II activity units of from about 50:50 to about 80:20.

15. A cell having ATCC accession number 55691.

16. A cell having ATCC accession number 55690.

17. A cell having ATCC accession number 55689.

18. A mutant cell as defined in claim 1, further comprising a chondroitinases I and II expression plasmid, wherein said plasmid directs the production of chondroitinases I and II in said cell.

19. A mutant cell as defined in claim 18, wherein said expression plasmid is $pLP^2 1531$.

20. A mutant cell as defined in claim 1, further comprising a chondroitinase I expression plasmid, wherein said plasmid directs production of chondroitinase I in said cell.

21. A mutant cell as defined in claim 20, wherein said expression plasmid is $pLP^2 1521$.

22. A method for producing *P. vulgaris* chondroitinase I and chondroitinase II proteins, said method comprising:

(a) culturing a mutant cell as defined in claim 1 in a bacterial culture medium and in the absence of an exogenous chondroitinases I and II inducer;

(b) harvesting said cells from said culture; and (c) recovering said chondroitinase I and chondroitinase II proteins from said harvested cells.

23. A method as defined in claim 22, wherein said culturing comprises growing said cell in a medium selected from the group consisting of rich medium and minimal medium containing glucose as a sole carbon source.

24. A method as defined in claim 22, wherein said recovering comprises
   (i) preparing a clarified homogenate of said harvested cells, said homogenate having a pH of 5.8 to 7.4;
   (ii) loading said homogenate onto a negatively charged cation exchange resin chromatographic support so that any positively charged proteins comprising chondroitinase I and chondroitinase II in said homogenate form a non-covalent bond with said negatively charged support;
   (iii) affinity-eluting, in pools, said chondroitinase proteins from the support with an aqueous solution of chondroitin sulfate at a pH 7.0–9.5;
   (iv) loading said affinity eluted protein pools from step (iii) onto an anion exchange resin chromatographic support to yield an unbound eluate; and
   (v) recovering the chondroitinase I and chondroitinase II proteins in the unbound eluate.

25. A method as defined in claim 24, wherein step (v) comprises:
   (1) contacting said unbound eluate with a metal chelating affinity chromatography support to bind further said chondroitinase proteins;
   (2) eluting with an appropriate solvent;
   (3) recovering said chondroitinase proteins.

* * * * *